US00PP08902P

United States Patent [19]

Denis

[11] Patent Number: Plant 8,902

[45] Date of Patent: Sep. 20, 1994

[54] *FICUS BENJAMINA* PLANT NAMED FRANCIS

[75] Inventor: Rene G. M. A. Denis, Destelbergen, Belgium

[73] Assignee: Denis-Plants B.V.B.A., Beervelde, Belgium

[21] Appl. No.: 120,445

[22] Filed: Sep. 14, 1993

[51] Int. Cl.[5] ..... A01H 5/00
[52] U.S. Cl. ..... Plt./88.9
[58] Field of Search ..... Plt. 88.9

*Primary Examiner*—James R. Feyrer
*Attorney, Agent, or Firm*—Foley & Lardner

[57] ABSTRACT

A new cultivar of *Ficus benjamina* named 'Francis', characterized by its unique leaf variegation, which includes dark green irregular markings along and radiating from the midrib, and a fresh white-yellow-light green variegation elsewhere, with the variegated markings maturing to a light to medium green which is always lighter than the dark green markings around the midrib, which comprise 30 to 50% of the leaf surface.

2 Drawing Sheets

The present invention comprises a new and distinct cultivar of *Ficus benjamina,* known by the cultivar name 'Francis'.

'Francis' is a mutation discovered by the inventor Rene G. M. A. Denis in greenhouses in Lochristi-Beervelde, Belgium in 1990. The new cultivar was discovered growing among plants of the parent cultivar *Ficus benjamina* 'Golden King', and was recognized due to its special leaf color. 'Golden King' is disclosed in U.S. Plant Pat. No. 6,460.

The first act of asexual reproduction of 'Francis' was accomplished by tissue culture later in 1990 in a laboratory in Lochristi-Beervelde, Belgium by applicant. Horticultural examination of 'Francis' has demonstrated that the combination of characteristics as herein disclosed for the new cultivar are firmly fixed and are retained through successive generations of asexual reproduction, which can be performed by cuttings in addition to tissue culture.

'Francis' has not been observed under all possible environmental conditions. The phenotype may vary somewhat with variations in environment such as temperature, light intensity, and day length, without, however, any variation in genotype. The following observations, measurements and comparisons describe plants grown in Lochristi-Beervelde, Belgium, under greenhouse conditions which closely approximate those generally used in horticultural practice.

The following traits have been repeatedly observed to be characteristics which in combination distinguish 'Francis' from other varieties of *Ficus benjamina* with which the inventor is familiar.

1. The surrounding color of 'Francis' is a fresh white-yellow-light green, with dark green variegation of varying dimension from the midrib to both sides or surrounding margins. The leaf color is totally different than the parent 'Golden King', which is much more yellow-grey, and also different from 'Starlight', where the surrounding color is white, and from other variegated varieties of *Ficus benjamina* with which applicant is familiar. At a particular time, the surrounding color of 'Francis' is about 10% white, 10% green and 80% yellow-light green. This provides a very fresh combination of colors.

2. New leaves have more yellow-light green surroundings, which turn to white for interior leaves covered by new ones. If leaves remain fully exposed to light they will maintain the fresh yellow-light green color. This can be seen in the photographs, where mature, fully exposed leaves are of the same color as newly formed leaves. Older leaves can turn to a light green, but this green surrounding is always lighter green when compared to the marking of darker green in the middle of the leaf. The leaves of 'Francis' are similar in size to 'Golden King', and longer and wider than the leaves of 'Starlight'.

3. 'Francis' has a green to dark green irregular marking along the midrib, which is similar to the color of other known *Ficus benjamina* types having variegated leaves. However, where this marking comprises 70 to 90% of the leaf surface of the parent 'Golden King', the marking of 'Francis' is restricted to 30 to 50% of the leaf surface. This means the color of the surroundings of the leaves of 'Francis' is much more significant compared to the parent 'Golden King', and can be compared with the surroundings of the *Ficus benjamina* 'Starlight'. However, where 'Starlight' has a white surroundings, those of 'Francis' are a combination of white, yellow and light green, as mentioned above.

4. The color of the midrib of 'Francis' is white to yellow or light green, the same as the surrounding leaf, and can be distinguished clearly from the dark green marking in the middle of the leaf. In contrast, the midrib of 'Starlight' is white and the midrib of 'Golden King' is grey-white. All three cultivars has relatively thick midribs and normal side veins extending from the midrib to the margin.

5. In comparison to known cultivars, 'Francis' is distinguished by its fresh white-yellow-light green color, which makes a beautiful combination with the darker green marking in the middle of the leaf to both sides of the midrib.

6. With regard to growth time, for tissue culture derived plants started in February, 'Golden King' requires 25 weeks to reach 90 cm. 'Francis' 28 weeks, and 'Starlight' 36 weeks. For plants started in September these periods are 30 weeks, 34 weeks, and 44 weeks, respectively. Thus, 'Francis' is somewhat slower than 'Golden King', but much faster than 'Starlight', roughly comparable to the quantities of chlorophyll in the leaves of the respective cultivars.

7. When compared to the parent 'Golden King', 'Francis' has a lighter surrounding, a smaller area of midrib marking, a lighter midrib color, slower growing time, more dense growth and shorter internode spacing, and its leaves are much more shiny.

8. When compared to 'Starlight', 'Francis' has a predominantly darker surrounding color, larger leaves, darker midrib color, and a much faster growth habit.

All color references are measured against The *Royal Horticultural Society Colour Chart*. Color may vary somewhat depending on horticultural practices such as light level, temperature, and fertilization rate, among others.

BRIEF DESCRIPTION OF THE DRAWING

The accompanying color photographic drawings illustrate a typical specimen plant of 'Francis', with photographic color depicting true colors to the extent possible with reproductions of this type.

The photograph at the top of sheet 1 comprises a comparison of branches taken from plants of 'Starlight' (on left), 'Francis' (center) and 'Golden King' (right). The plants are of comparable age and grown under the same conditions.

The photo on the bottom of sheet 1 shows individual leaves of 'Francis' and the comparison cultivars, with both young and older leaves of 'Francis' being illustrated. The colors shown in this photo fairly closely depict the color values for new and older leaves noted below.

The photo of sheet 2 is somewhat enlarged and shows both new and older leaves of 'Francis' in greater number and detail.

DETAILED BOTANICAL DESCRIPTION

Origin: Mutation discovered among tissue culture-derived plants of *Ficus benjamina* 'Golden King'.

Classification: *Ficus benjamina* c.v. 'Francis'.

Propagation: By cutting or tissue culture.

Plant: The plant has the usual *Ficus benjamina shape, similar to 'Golden King' and 'Starlight'. The main stem is irregularly branched, with the branches being at an angle of* 45° to 60° and the tips bending down. Older branches are nearly horizontal.

Bark: The bark of 'Francis' is similar to the bark of 'Golden King' and 'Starlight'.

Leaves:

*Shape.*—Elliptic to acuminate with a rather long pointed tip.

*Size.*—8 to 10 cm long, 3.5 to 4 cm wide.

*Quantity.*—Very dense leaf production due to internode spacing of 1.5 to 2.5 cm, occasionally 3 cm. Leaf production is much greater than 'Golden King' and comparable to 'Starlight'.

*Margin.*—Smooth.

*Aspect.*—The surface of the leaf is slightly undulating or wavy.

*Texture.*—Slightly glossy, luxuriant.

*Petiole.*—About 1.5 to 2 cm long.

*Veins.*—A rather thick midrib and normal side veins extending from midrib to margin color of midrib is same as surrounding color for both young and mature leaves.

*Variegation.*—Along and extending laterally from the midrib are dark green irregular markings that occupy 30 to 70% of the total leaf surface.

*Color.*—Upper surface: The color of the youngest leaves is a mixture of yellow and green. The lightest color is 144 A, variegated with 147 B, with darkest part of the leaf being 137 A. Older leaves change in color due to maturity, less light, or being covered by younger leaves. The amounts of varying colors in such circumstances will vary, with 157 A, 191 A–193 A and 189 A all being present. All those values appear on various leaves in the photo on sheet 2. Lower surface: The color on the lower surface of the older leaves is 145 C. The green variegation is between 191 A and 137 C. For younger leaves the yellow-green color is 144 B, while the green is 137 D. Upper surface midrib: The upper surface midrib of oldest leaves is between light green and 157 A. For younger leaves this color is more light green 145 C. Lower surface midrib: The lower surface midrib has the same color as the upper surface midrib, 157 A for older leaves and 145 C for younger leaves. Petiole: The color of the petiole is 146 B. Branches are 200 D.

Inflorescence: Insignificant.

Reproductive organs: Normal.

Roots: Good rooting system.

Fig production: 'Francis' has not been observed to produce figs, nor has 'Golden King' or 'Starlight'.

I claim:

1. A new and distinct cultivar of *Ficus benjamina* named 'Francis', as illustrated and described.

* * * * *

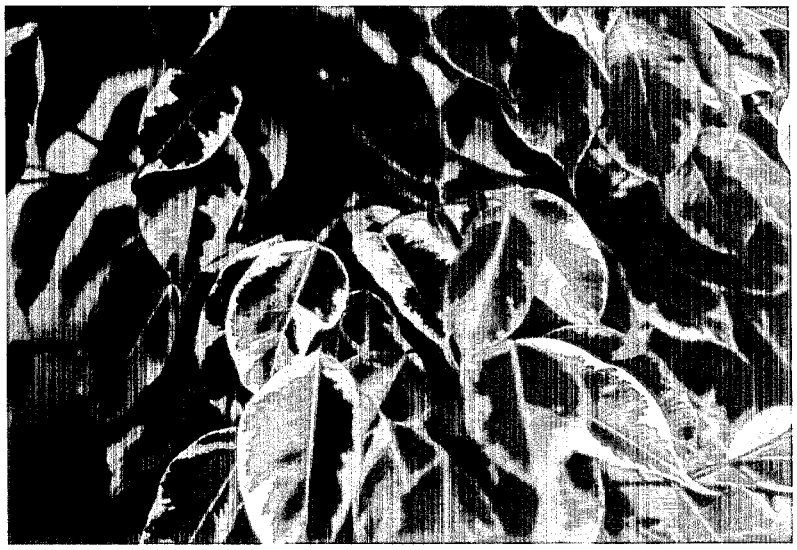

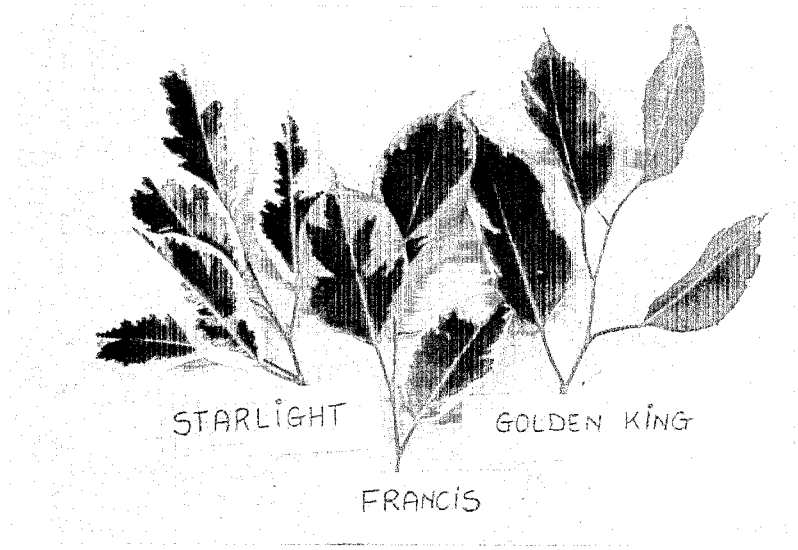
STARLIGHT
GOLDEN KING
FRANCIS
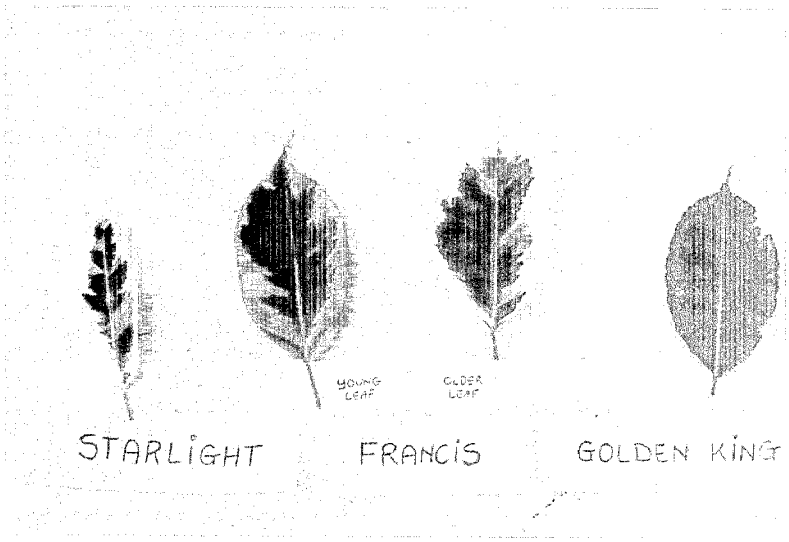
YOUNG LEAF
OLDER LEAF
STARLIGHT
FRANCIS
GOLDEN KING